United States Patent
Lee et al.

(10) Patent No.: US 11,882,837 B2
(45) Date of Patent: Jan. 30, 2024

(54) METHOD AND COMPOSITION COMPRISING DETOXIFIED LIPOPOLYSACCHARIDE AND LIPOTEICHOIC ACID FOR PREVENTING OR INHIBITING FORMATION OF BIOFILM

(71) Applicants: SOGANG UNIVERSITY RESEARCH & BUSINESS DEVELOPMENT FOUNDATION, Seoul (KR); KOREA FOOD & DRUG ADMINISTRATION, Cheongju-si (KR)

(72) Inventors: Kyu-Ho Lee, Seoul (KR); Hyo-Sun Kwak, Cheongju-si (KR); Youchul Jung, Gimhae-si (KR); Kyung Jo Lee, Seoul (KR); Jeong-A Kim, Seoul (KR); Boram Jang, Incheon (KR); Sebin Kang, Gwacheon-si (KR)

(73) Assignees: SOGANG UNIVERSITY RESEARCH & BUSINESS DEVELOPMENT FOUNDATION, Seoul (KR); KOREA FOOD & DRUG ADMINISTRATION, Cheongju-si (KR)

( * ) Notice: Subject to any disclaimer, the term of this patent is extended or adjusted under 35 U.S.C. 154(b) by 1134 days.

(21) Appl. No.: 16/577,944

(22) Filed: Sep. 20, 2019

(65) Prior Publication Data
US 2020/0163341 A1    May 28, 2020

(30) Foreign Application Priority Data
Nov. 22, 2018  (KR) .................... 10-2018-0145153

(51) Int. Cl.
| | | |
|---|---|---|
| A01N 63/10 | (2020.01) | |
| A61L 2/00 | (2006.01) | |
| A01N 1/00 | (2006.01) | |
| A01N 63/20 | (2020.01) | |
| A61K 35/66 | (2015.01) | |
| A61K 35/74 | (2015.01) | |
| A61K 36/00 | (2006.01) | |
| A61P 31/04 | (2006.01) | |
| C12N 1/20 | (2006.01) | |
| C12P 39/00 | (2006.01) | |
| C12R 1/01 | (2006.01) | |
| C12R 1/025 | (2006.01) | |
| C12N 1/00 | (2006.01) | |

(52) U.S. Cl.
CPC ................ *A01N 63/10* (2020.01); *A01N 1/00* (2013.01); *A01N 63/20* (2020.01); *A61K 35/66* (2013.01); *A61K 35/74* (2013.01); *A61K 36/00* (2013.01); *A61L 2/00* (2013.01); *C12N 1/20* (2013.01); *C12N 1/205* (2021.05); *C12P 39/00* (2013.01); *A61P 31/04* (2018.01); *C12N 1/00* (2013.01); *C12R 2001/01* (2021.05); *C12R 2001/025* (2021.05)

(58) Field of Classification Search
CPC ....................................................... A61N 1/00
See application file for complete search history.

(56) References Cited

FOREIGN PATENT DOCUMENTS

| | | | | |
|---|---|---|---|---|
| PH | 12012501540 B1 | * | 3/2016 | ........... A23L 33/135 |
| WO | WO-2012142605 A1 | * | 10/2012 | ........... A23L 1/3014 |

OTHER PUBLICATIONS

Lee et al., "Deacylated lipopolysaccharides inhibit biofilm formation by Gram-negative bacteria", Biofouling, (2016), vol. 32, No. 7, pp. 711-723.

* cited by examiner

*Primary Examiner* — Gina C Justice
(74) *Attorney, Agent, or Firm* — Vorys, Sater, Seymour and Pease LLP; Mih Suhn Koh (57) ABSTRACT

Provided is a novel bacterial strain *Bacteroides vulgatus* MGM001 (*Bacteroides vulgatus* MGM001) and its use. The LPS from the strain of the subject matter has cytotoxicity weaker than the conventional ones and shows synergistic effect on the inhibition of biofilm formation when used in combination with LTA.

7 Claims, 7 Drawing Sheets

Specification includes a Sequence Listing.

FIG. 1A

| | | |
|---|---|---|
| mpk | (SEQ ID NO: 2) | CCTTGTTACGACTTAGCCCCAGTCACCAGTTTTACCCTAGGGCGCTCCTCGCGGTTACGC |
| JCM | (SEQ ID NO: 3) | CCTTGTTACGACTTAGCCCCAGTCACCAGTTTTACCCTAGGGCGCTCCTCGCGGTTACGC |
| BCRC12903 | (SEQ ID NO: 4) | CCTTGTTACGACTTAGCCCCAGTCACCAGTTTTACCCTAGGGCGCTCCTCGCGGTTACGC |
| ATCC8482 | (SEQ ID NO: 5) | CCTTGTTACGACTTAGCCCCAGTCACCAGTTTTACCCTAGGGCGCTCCTCGCGGTTACGC |
| MGM001 | (SEQ ID NO: 1) | CCTT-TGACGACTTAGCCCCAGTCACCAGTTTTACCCTAGGGCGCTCCTCGCGGTTACGC |
| | | **** * ***************************************************** |

| | | |
|---|---|---|
| mpk | (SEQ ID NO: 2) | ACTTCAGGTACCCCCGGCTCCCATGGCTTGACGGGCGGTGTGTACAAGGCCCGGGAACGT |
| JCM | (SEQ ID NO: 3) | ACTTCAGGTACCCCCGGCTCCCATGGCTTGACGGGCGGTGTGTACAAGGCCCGGGAACGT |
| BCRC12903 | (SEQ ID NO: 4) | ACTTCAGGTACCCCCGGCTCCCATGGCTTGACGGGCGGTGTGTACAAGGCCCGGGAACGT |
| ATCC8482 | (SEQ ID NO: 5) | ACTTCAGGTACCCCCGGCTCCCATGGCTTGACGGGCGGTGTGTACAAGGCCCGGGAACGT |
| MGM001 | (SEQ ID NO: 1) | ACTTCAGGTACCCCGGCTCCCATGGCTTGACGGGCGGTGTGTACAAGGCCCGGGAACGT |
| | | ************************************************************ |

| | | |
|---|---|---|
| mpk | (SEQ ID NO: 2) | ATTCACCGCGCCGTGGCTGATGCGCGATTACTAGCGAATCCAGCTTCGTGGAGTCGGGTT |
| JCM | (SEQ ID NO: 3) | ATTCACCGCGCCGTGGCTGATGCGCGATTACTAGCGAATCCAGCTTCGTGGAGTCGGGTT |
| BCRC12903 | (SEQ ID NO: 4) | ATTCACCGCGCCGTGGCTGATGCGCGATTACTAGCGAATCCAGCTTCGTGGAGTCGGGTT |
| ATCC8482 | (SEQ ID NO: 5) | ATTCACCGCGCCGTGGCTGATGCGCGATTACTAGCGAATCCAGCTTCGTGGAGTCGGGTT |
| MGM001 | (SEQ ID NO: 1) | ATTCACCGCGCCGTGGCTGATGCGCGATTACTAGCGAATCCAGCTTCGTGGAGTCGGGTT |
| | | ************************************************************ |

| | | |
|---|---|---|
| mpk | (SEQ ID NO: 2) | GCAGACTCCAGTCCGAACTGAGAGAGGTTTTGGGGATTGGCATCCACTCGCGTGGTAGCG |
| JCM | (SEQ ID NO: 3) | GCAGACTCCAGTCCGAACTGAGAGAGGTTTTGGGGATTGGCATCCACTCGCGTGGTAGCG |
| BCRC12903 | (SEQ ID NO: 4) | GCAGACTCCAGTCCGAACTGAGAGAGGTTTTGGGGATTGGCATCCACTCGCGTGGTAGCG |
| ATCC8482 | (SEQ ID NO: 5) | GCAGACTCCAGTCCGAACTGAGAGAGGTTTTTGGGATTGGCATCCACTCGCGTGGTAGCG |
| MGM001 | (SEQ ID NO: 1) | GCAGACTCCAGTCCGAACTGAGAGAGGTTTTTGGGATTGGCATCCACTCGCGTGGTAGCG |
| | | ******************************* ************************** |

| | | |
|---|---|---|
| mpk | (SEQ ID NO: 2) | GCCCTCTGTACCCCCCATTGTAACACGTGTGTAGCCCCGGACGTAAGGGCCGTGCTGATT |
| JCM | (SEQ ID NO: 3) | GCCCTCTGTACCCCCCATTGTAACACGTGTGTAGCCCCGGACGTAAGGGCCGTGCTGATT |
| BCRC12903 | (SEQ ID NO: 4) | GCCCTCTGTACCCCCCATTGTAACACGTGTGTAGCCCCGGACGTAAGGGCCGTGCTGATT |
| ATCC8482 | (SEQ ID NO: 5) | GCCCTCTGTACCCCCCATTGTAACACGTGTGTAGCCCCGGACGTAAGGGCCGTGCTGATT |
| MGM001 | (SEQ ID NO: 1) | GCCCTCTGTACCCCCCATTGTAACACGTGTGTAGCCCCGGACGTAAGGGCCGTGCTGATT |
| | | ************************************************************ |

| | | |
|---|---|---|
| mpk | (SEQ ID NO: 2) | TGACGTCATCCCCACCTTCCTCACATCTTACGATGGCAGTCTTGTCAGAGTCCTCAGCCG |
| JCM | (SEQ ID NO: 3) | TGACGTCATCCCCACCTTCCTCACATCTTACGATGGCAGTCTTGTCAGAGTCCTCAGCAT |
| BCRC12903 | (SEQ ID NO: 4) | TGACGTCATCCCCACCTTCCTCACATCTTACGATGGCAGTCTTGTCAGAGTCCTCAGCAT |
| ATCC8482 | (SEQ ID NO: 5) | TGACGTCATCCCCACCTTCCTCACATCTTACGATGGCAGTCTTGTCAGAGTCCTCAGCAG |
| MGM001 | (SEQ ID NO: 1) | TGACGTCATCCCCACCTTCCTCACATCTTACGATGGCAGTCTTGTCAGAGTCCTCAGCAG |
| | | ********************************************************* * |

| | | |
|---|---|---|
| mpk | (SEQ ID NO: 2) | AACCTGTTAGTAACTGACAACAAGGGTTGCGCTCGTTATGGCACTTAAGCCGACACCTCA |
| JCM | (SEQ ID NO: 3) | AACCTGTTAGTAACTGACAACAAGGGTTGCGCTCGTTATGGCACTTAAGCCGACACCTCA |
| BCRC12903 | (SEQ ID NO: 4) | GACCTGTTAGTAACTGACAACAAGGGTTGCGCTCGTTATGGCACTTAAGCCGACACCTCA |
| ATCC8482 | (SEQ ID NO: 5) | AACCTGTTAGTAACTGACAACAAGGGTTGCGCTCGTTATGGCACTTAAGCCGACACCTCA |
| MGM001 | (SEQ ID NO: 1) | AACCTGTTAGTAACTGACAACAAGGGTTGCGCTCGTTATGGCACTTAAGCCGACACCTCA |
| | | *********************************************************** |

FIG. 1B

| | | |
|---|---|---|
| mpk | (SEQ ID NO: 2) | CGGCACGAGCTGACGACAACCATGCAGCACCTTCACAGATGCCTTGCCGGCTTACGGCTTT |
| JCM | (SEQ ID NO: 3) | CGGCACGAGCTGACGACAACCATGCAGCACCTTCACAGATGCCTTGCCGGCTTACGGCTTT |
| BCRC12903 | (SEQ ID NO: 4) | CGGCACGAGCTGACGACAACCATGCAGCACCTTCACAGATGCCTTGCCGGCTTACGGCTTT |
| ATCC8482 | (SEQ ID NO: 5) | CGGCACGAGCTGACGACAACCATGCAGCACCTTCACAGATGCCTTGCCGGCTTACGGCTTT |
| MGM001 | (SEQ ID NO: 1) | CGGCACGAGCTGACGACAACCATGCAGCACCTTCACAGATGCCTTGCCGGCTTACGGCTTT |
| | | ************************************************************ |

| | | |
|---|---|---|
| mpk | (SEQ ID NO: 2) | CACCGTAATTCATCTGCAATTTAAGCCCGGGTAAGGTTCCTCGCGTATCATCGAATTAAA |
| JCM | (SEQ ID NO: 3) | CACCGTAATTCATCTGCAATTTAAGCCCGGGTAAGGTTCCTCGCGTATCATCGAATTAAA |
| BCRC12903 | (SEQ ID NO: 4) | CACCGTAATTCATCTGCAATTTAAGCCCGGGTAAGGTTCCTCGCGTATCATCGAATTAAA |
| ATCC8482 | (SEQ ID NO: 5) | CACCGTAATTCATCTGCAATTTAAGCCCGGGTAAGGTTCCTCGCGTATCATCGAATTAAA |
| MGM001 | (SEQ ID NO: 1) | CACCGTAATTCATCTGCAATTTAAGCCCGGGTAAGGTTCCTCGCGTATCATCGAATTAAA |
| | | ************************************************************ |

| | | |
|---|---|---|
| mpk | (SEQ ID NO: 2) | CCACATGTTCCTCCGCTTGTGCGGGCCCCGTCAATTCCTTTGAGTTTCACCGTTGCCGG |
| JCM | (SEQ ID NO: 3) | CCACATGTTCCTCCGCTTGTGCGGGCCCCGTCAATTCCTTTGAGTTTCACCGTTGCCGG |
| BCRC12903 | (SEQ ID NO: 4) | CCACATGTTCCTCCGCTTGTGCGGGCCCCGTCAATTCCTTTGAGTTTCACCGTTGCCGG |
| ATCC8482 | (SEQ ID NO: 5) | CCACATGTTCCTCCGCTTGTGCGGGCCCCGTCAATTCCTTTGAGTTTCACCGTTGCCGG |
| MGM001 | (SEQ ID NO: 1) | CCACATGTTCCTCCGCTTGTGCGGGCCCCGTCAATTCCTTTGAGTTTCACCGTTGCCGG |
| | | ************************************************************ |

| | | |
|---|---|---|
| mpk | (SEQ ID NO: 2) | CGTACTCCCCAGGTGGAATACTTAACGCTTTCGCTTGGCCGCTTGCAGTATATCGCAAAC |
| JCM | (SEQ ID NO: 3) | CGTACTCCCCAGGTGGAATACTTAACGCTTTCGCTTGGCCGCTTGCCGTATATCGCAAAC |
| BCRC12903 | (SEQ ID NO: 4) | CGTACTCCCCAGGTGGAATACTTAACGCTTTCGCTTGGCCGCTTGCCGTATATCGCAAAC |
| ATCC8482 | (SEQ ID NO: 5) | CGTACTCCCCAGGTGGAATACTTAACGCTTTCGCTTGGCCGCTTGCCGTATATCGCAAAC |
| MGM001 | (SEQ ID NO: 1) | CGTACTCCCCAGGTGGAATACTTAACGCTTTCGCTTGGCCGCTTGCCGTATATCGCAAAC |
| | | ******************************************** ************* |

| | | |
|---|---|---|
| mpk | (SEQ ID NO: 2) | AGCGAGTATTCATCGTTTACCGTGTGGACTACCAGGGTATCTAATCCTGTTTGATACCCA |
| JCM | (SEQ ID NO: 3) | AGCGAGTATTCATCGTTTACCGTGTGGACTACCAGGGTATCTAATCCTGTTTGATACCCA |
| BCRC12903 | (SEQ ID NO: 4) | AGCGAGTATTCATCGTTTACCGTGTGGACTACCAGGGTATCTAATCCTGTTTGATACCCA |
| ATCC8482 | (SEQ ID NO: 5) | AGCGAGTATTCATCGTTTACCGTGTGGACTACCAGGGTATCTAATCCTGTTTGATACCCA |
| MGM001 | (SEQ ID NO: 1) | AGCGAGTATTCATCGTTTACCGTGTGGACTACCAGGGTATCTAATCCTGTTTGATACCCA |
| | | ************************************************************ |

| | | |
|---|---|---|
| mpk | (SEQ ID NO: 2) | CACTTTCGAGCCTCAATGTCAGTTGCAGCTTAGCAGGCTGCCTTCGCAATCGGAGTTCTT |
| JCM | (SEQ ID NO: 3) | CACTTTCGAGCCTCAATGTCAGTTGCAGCTTAGCAGGCTGCCTTCGCAATCGGAGTTCTT |
| BCRC12903 | (SEQ ID NO: 4) | CACTTTCGAGCCTCAATGTCAGTTGCAGCTTAGCAGGCTGCCTTCGCAATCGGAGTTCTT |
| ATCC8482 | (SEQ ID NO: 5) | CACTTTCGAGCCTCAATGTCAGTTGCAGCTTAGCAGGCTGCCTTCGCAATCGGAGTTCT |
| MGM001 | (SEQ ID NO: 1) | CACTTTCGAGCCTCAATGTCAGTTGCAGCTTAGCAGGCTGCCTTCGCAATCGGAGTTCTT |
| | | *********************************************************  * |

| | | |
|---|---|---|
| mpk | (SEQ ID NO: 2) | CGTGATATCTAAGCATTTCACCGCTACACCACGAATTCCGCCTGCCTCAACTGCACTCAA |
| JCM | (SEQ ID NO: 3) | CGTGATATCTAAGCATTTCACCGCTACACCACGAATTCCGCCTGCCTCAACTGCACTCAA |
| BCRC12903 | (SEQ ID NO: 4) | CGTGATATCTAAGCATTTCACCGCTACACCACGAATTCCGCCTGCCTCAACTGCACTCAA |
| ATCC8482 | (SEQ ID NO: 5) | CGTGATATCTAAGCATTTCACCGCTACACCACGAATTCCGCCTGCCTCAACTGCACTCAA |
| MGM001 | (SEQ ID NO: 1) | CGTGATATCTAAGCATTTCACCGCTACACCACGAATTCCGCCTGCCTCAACTGCACTCAA |
| | | ************************************************************ |

FIG. 1C

```
mpk        (SEQ ID NO: 2)  GATATCCAGTATCAACTGCAATTTTACGGTTGAGCCGCAAACTTTCACAACTGACTTAAA
JCM        (SEQ ID NO: 3)  GATATCCAGTATCAACTGCAATTTTACGGTTGAGCCGCAAACTTTCACAACTGACTTAAA
BCRC12903  (SEQ ID NO: 4)  GATATCCAGTATCAACTGCAATTTTACGGTTGAGCCGCAAACTTTCACAACTGACTTAAA
ATCC8482   (SEQ ID NO: 5)  GATATCCAGTATCAACTGCAATTTTACGGTTGAGCCGCAAACTTTCACAACTGACTTAAA
MGM001     (SEQ ID NO: 1)  GATATCCAGTATCAACTGCAATTTTACGGTTGAGCCGCAAACTTTCACAACTGACTTAAA
                           ************************************************************ mpk        (SEQ ID NO: 2)  CATCCATCTACGCTCCCTTTAAACCCAATAAATCCGGATAACGCTCGGATCCTCCGTATT
JCM        (SEQ ID NO: 3)  CATCCATCTACGCTCCCTTTAAACCCAATAAATCCGGATAACGCTCGGATCCTCCGTATT
BCRC12903  (SEQ ID NO: 4)  CATCCATCTACGCTCCCTTTAAACCCAATAAATCCGGATAACGCTCGGATCCTCCGTATT
ATCC8482   (SEQ ID NO: 5)  CATCCATCTACGCTCCCTTTAAACCCAATAAATCCGGATAACGCTCGGATCCTCCGTATT
MGM001     (SEQ ID NO: 1)  CATCCATCTACGCTCCCTTTAAACCCAATAAATCCGGATAACGCTCGGATCCTCCGTATT
                           ************************************************************ mpk        (SEQ ID NO: 2)  ACCGCGGCTGCTGGCACGGAGTTAGCCGATCCTTATTCATAAAGTACATGCAAACGGGTA
JCM        (SEQ ID NO: 3)  ACCGCGGCTGCTGGCACGGAGTTAGCCGATCCTTATTCATAAAGTACATGCAAACGGGTA
BCRC12903  (SEQ ID NO: 4)  ACCGCGGCTGCTGGCACGGAGTTAGCCGATCCTTATTCATAAAGTACATGCAAACGGGTA
ATCC8482   (SEQ ID NO: 5)  ACCGCGGCTGCTGGCACGGAGTTAGCCGATCCTTATTCATAAAGTACATGCAAACGGGTA
MGM001     (SEQ ID NO: 1)  ACCGCGGCTGCTGGCACGGAGTTAGCCGATCCTTATTCATAAAGTACATGCAAACGGGTA
                           ************************************************************ mpk        (SEQ ID NO: 2)  TCCATACCCGACTTTATTCCTTTATAAAAGAAGTTTACAACCCATAGGGCAGTCATCCTT
JCM        (SEQ ID NO: 3)  TCCATACCCGACTTTATTCCTTTATAAAAGAAGTTTACAACCCATAGGGCAGTCATCCTT
BCRC12903  (SEQ ID NO: 4)  TCCATACCCGACTTTATTCCTTTATAAAAGAAGTTTACAACCCATAGGGCAGTCATCCTT
ATCC8482   (SEQ ID NO: 5)  TGCATACCCGACTTTATTCCTTTATAAAAGAAGTTTACAACCCATAGGGCAGTCATCCTT
MGM001     (SEQ ID NO: 1)  TCCATACCCGACTTTATTCCTTTATAAAAGAAGTTTACAACCCATAGGGCAGTCATCCTT
                           * ********************************************************** mpk        (SEQ ID NO: 2)  CACGCTACTTGGCTGGTTCAGGCTCTCGCCCATTGACCAATATTCCTCACTGCTGCCTCC
JCM        (SEQ ID NO: 3)  CACGCTACTTGGCTGGTTCAGGCTCTCGCCCATTGACCAATATTCCTCACTGCTGCCTCC
BCRC12903  (SEQ ID NO: 4)  CACGCTACTTGGCTGGTTCAGGCTCTCGCCCATTGACCAATATTCCTCACTGCTGCCTCC
ATCC8482   (SEQ ID NO: 5)  CACGCTACTTGGCTGGTTCAGGCTCTCGCCCATTGACCAATATTCCTCACTGCTGCCTCC
MGM001     (SEQ ID NO: 1)  CACGCTACTTGGCTGGTTCAGGCTCTCGCCCATTGACCAATATTCCTCACTGCTGCCTCC
                           ************************************************************ mpk        (SEQ ID NO: 2)  CGTAGGAGTTTGGACCGTGTCTCAGTTCCAATGTGGGGGACCTTCCTCTCAGAACCCCTA
JCM        (SEQ ID NO: 3)  CGTAGGAGTTTGGACCGTGTCTCAGTTCCAATGTGGGGGACCTTCCTCTCAGAACCCCTA
BCRC12903  (SEQ ID NO: 4)  CGTAGGAGTTTGGACCGTGTCTCAGTTCCAATGTGGGGGACCTTCCTCTCAGAACCCCTA
ATCC8482   (SEQ ID NO: 5)  CGTAGGAGTTTGGACCGTGTCTCAGTTCCAATGTGGGGGACCTTCCTCTCAGAACCCCTA
MGM001     (SEQ ID NO: 1)  CGTAGGAGTTTGGACCGTGTCTCAGTTCCAATGTGGGGGACCTTCCTCTCAGAACCCCTA
                           ************************************************************ mpk        (SEQ ID NO: 2)  TCCATCGAAGACTAGGTGGGCCGTTACCCCGCCTACTATCTAATGGAACGCATCCCCATC
JCM        (SEQ ID NO: 3)  TCCATCGAAGACTAGGTGGGCCGTTACCCCGCCTACTATCTAATGGAACGCATCCCCATC
BCRC12903  (SEQ ID NO: 4)  TCCATCGAAGACTAGGTGGGCCGTTACCCCGCCTACTATCTAATGGAACGCATCCCCATC
ATCC8482   (SEQ ID NO: 5)  TCCATCGAAGACTAGGTGGGCCGTTACCCCGCCTACTATCTAATGGAACGCATCCCCATC
MGM001     (SEQ ID NO: 1)  TCCATCGAAGACTAGGTGGGCCGTTACCCCGCCTACTATCTAATGGAACGCATCCCCATC
                           ************************************************************
```

FIG. 1D

```
mpk        (SEQ ID NO: 2)  GTCTACCGGAATACCTTTAATCATGTGAACATGCGGACTCATGATGCCATCTTGTATTAA
JCM        (SEQ ID NO: 3)  GTCTACCGGAATACCTTTAATCATGTGAACATGCGGACTCATGATGCCATCTTGTATTAA
BCRC12903  (SEQ ID NO: 4)  GTCTACCGGAATACCTTTAATCATGTGAACATGCGGACTCATGATGCCATCTTGTATTAA
ATCC8482   (SEQ ID NO: 5)  GTCTACCGGAATACCTTTAATCATGTGAACATGCGGACTCATGATGCCATCTTGTATTAA
MGM001     (SEQ ID NO: 1)  GTCTACCGGAATACCTTTAATCATGTGAACATGCGGACTCATGATGCCATCTTGTATTAA
                           ************************************************************ mpk        (SEQ ID NO: 2)  TCTTCCTTTCAGAAGGCTGTCCAAGAGTAGACGGCAGGTTGGATACGTGTTACTCACCCG
JCM        (SEQ ID NO: 3)  TCTTCCTTTCAGAAGGCTGTCCAAGAGTAGACGGCAGGTTGGATACGTGTTACTCACCCG
BCRC12903  (SEQ ID NO: 4)  TCTTCCTTTCAGAAGGCTGTCCAAGAGTAGACGGCAGGTTGGATACGTGTTACTCACCCG
ATCC8482   (SEQ ID NO: 5)  TCTTCCTTTCAGAAGGCTGTCCAAGAGTAGACGGCAGGTTGGATACGTGTTACTCACCCG
MGM001     (SEQ ID NO: 1)  TCTTCCTTTCAGAAGGCTGTCCAAGAGTAGACGGCAGGTTGGATACGTGTTACTCACCCG
                           ************************************************************ mpk        (SEQ ID NO: 2)  TGCGCCGGTCGCCATCGGCCTTAGCAAGCTAAGACCATGCTGCCCCTCGACTTGCATGTG
JCM        (SEQ ID NO: 3)  TGCGCCGGTCGCCATCGGCCTTAGCAAGCTAAGACCATGCTGCCCCTCGACTTGCATGTG
BCRC12903  (SEQ ID NO: 4)  TGCGCCGGTCGCCATCGGCCTTAGCAAGCTAAGACCATGCTGCCCCTCGACTTGCATGTG
ATCC8482   (SEQ ID NO: 5)  TGCGCCGGTCGCCATCGGCCTTAGCAAGCTAAGACCATGCTGCCCCTCGACTTGCATGTG
MGM001     (SEQ ID NO: 1)  TGCGCCGGTCGCCATCGGCCTTAGCAAGCTAAGACCATGCTGCCCCTCGACTTGCATGTG
                           ************************************************************ mpk        (SEQ ID NO: 2)  TTAAGCCTGTAGCTAGCGTTCATCCTG
JCM        (SEQ ID NO: 3)  TTAAGCCTGTAGCTAGCGTTCATCCTG
BCRC12903  (SEQ ID NO: 4)  TTAAGCCTGTAGCTAGCGTTCATCCTG
ATCC8482   (SEQ ID NO: 5)  TTAAGCCTGTAGCTAGCGTTCATCCTG
MGM001     (SEQ ID NO: 1)  TTAAGCCTGTAGCTAGCGTTCATCCTG
                           ***************************
```

METHOD AND COMPOSITION COMPRISING DETOXIFIED LIPOPOLYSACCHARIDE AND LIPOTEICHOIC ACID FOR PREVENTING OR INHIBITING FORMATION OF BIOFILM

STATEMENT OF GOVERNMENT SUPPORT

The invention was made with government support under grant number 14162MFDS972 "Food-borne pathogen Omics Research Center" awarded by the Ministry of Food and Drug Safety, Republic of Korea.

CROSS-REFERENCE TO RELATED APPLICATIONS

This application claims the benefit of Korean Patent Application NO. 2018-0145153 filed Nov. 22, 2018 in the Korean Intellectual Property Office, disclosure of which is incorporated herein by reference.

SEQUENCE LISTING

The Sequence Listing submitted in text format (.txt) filed on Sep. 20, 2019, named "SequenceListing.txt", created on Sep. 18, 2019 (10.2 KB), is incorporated herein by reference.

BACKGROUND OF THE INVENTION

Field of the Invention

The present disclosure relates to method and composition to prevent or inhibit biofilm formation.

Description of the Related Art

More than 80% of pathogenic microorganisms produce biofilms and attach to and grow on the surface of human tissues, teeth, or medical prosthesis by forming colonies. Because of these characteristics, biofilms are known to be associated with numerous chronic infectious diseases. When biofilms are formed, various serious diseases such as endocarditis, sinusitis, periodontitis, tonsillitis and pneumonia are developed. Bacteria that form biofilms are at least 1,000 times more antibiotic resistant than bacteria that do not form biofilms. The bacterial biofilm formation is also closely related to the increase in the emergence of antibiotic resistant strains.

Therefore, there is a need for a solution that can fundamentally solve the biofilm formation by pathogenic bacteria. It is known that LPS (Lipopolysaccharide) extracted from *Vibrio vulnificus* and LTA (Lipoteichoic acid) extracted from *Staphylococcus aureus* inhibit the biofilm formation of Gram-negative and Gram-positive bacteria, respectively (Lee K J, et al. (2016) Biofouling. 32:711-723). However, LPS extracted from *V. vulnificus* and LTA extracted from *S. aureus* are difficult to use in real life in that they are extracted from strains that cause serious food poisoning in the human body. In addition, the anti-biofilm effect by LPS and LTA derived from other strains or dLPS and dLTA derived therefrom is not known yet.

SUMMARY OF THE INVENTION

Therefore, there exist needs to develop safe LPS and LTA extracted from human intestinal microorganisms beneficial to humans and detoxified dLPS and dLTA therefrom, and to verify their activity against biofilm formation in alone or in combination thereof. Further there is a need to develop a minimum concentration required to inhibit the biofilm formation in consideration of the high cost of dLPS and dLTA in which the cost of commercialized dLPS exceeds about 700 USD per 5 mg, and dLTA has no commercialized product available and LTA costs more than 170 USD per 5 mg.

In one aspect, there is provided isolated *Bacteroides vulgatus* MGM001 deposited as KCTC13624BP deposited Aug. 16, 2018 in Korean Collection for Type Cultures.

In other aspect, there is provided a method and composition comprising dLPS (deacylated Lipopolysaccharide) derived from the above described microorganism and dLTA (deacylated Lipoteichoic acid) in combination for prevent or inhibit biofilm formation.

In the foregoing method and composition, the dLTA is from intestinal *lactobacillus* such as *Lactobacillus plantarum*

Still in the foregoing method and composition, the dLPS and dLTA are comprised or used at the concentration ($\mu$g/ml) ratio of about 13.9:1.

Still in the foregoing method and compositions, the biofilms formed by Gram-positive as well as Gram-negative bacteria can be treated by the present method and composition to inhibit or reduce biofilm formation. In particular, the Gram-negative bacteria include *V. vulnificus*, and *P. aeruginosa*, the Gram-positive bacteria includes *S. aureus*, and *L. monocytogenes*.

In other aspect, there is provided a method to prevent or inhibit biofilm formation in vitro comprising treating Gram-positive or Gram-negative bacteria with the present composition.

In the foregoing methods, the contact with the bacteria includes treating the present composition on the surface selected from the surface made of Glaze ceramic, porcelain, glass, metal, wood, chrome, plastic, vinyl and fomica. In particularly. the surface made of acryl are excluded.

The foregoing summary is illustrative only and is not intended to be in any way limiting. Additional aspects and/or advantages of the invention will be set forth in part in the description which follows and, in part, will be obvious from the description, or may be learned by practice of the invention.

The present method and composition comprising detoxified dLPS and dLTA from intestinal microorganism beneficial to human in combination exerts synergistic effect to prevent or inhibit biofilm formation when they are used in combination. The superior effects of detoxified LPS and LTA can reduce the use of antibiotics per se and/or the amount of antibiotics used, reducing the overuse of antibiotics and minimizing the emergence of antibiotic resistant bacterial strain.

BRIEF DESCRIPTION OF THE DRAWINGS

These and/or other aspects and advantages of the invention will become apparent and more readily appreciated from the following description of the embodiments, taken in conjunction with the accompanying drawings of which:

FIGS. 1A-1D show the sequence of 16s rRNA of *Bacteroides vulgatus* MGM001 strain isolated herein, indicating that the strain isolated herein is novel. The sequence is aligned and compared to those from other strains of *Bacteroides vulgatus* as follows: *Bacteroides vulgatus* strain mpk (Mouse fecal isolate); *Bacteroides vulgatus* strain JCM 5826

(Human fecal isolate); *Bacteroides vulgatus* strain BCRC 12903 (Human fecal isolate); and *Bacteroides vulgatus* strain ATCC 8482 (Human fecal isolate). *Bacteroides vulgatus* is one of the major bacteria that constitutes intestinal microflora.

DETAILED DESCRIPTION OF THE EMBODIMENTS

The present disclosure is based, in part, on the discovery of novel strain of bacterium and LPS therefrom in combination with LTA can exert synergistic effect to inhibit biofilm formation particularly when they used in combination.

In one aspect, the present disclosure relates to *Bacteroides vulgatus* MGM001 deposited as KCTC13624BP Aug. 16, 2018 in Korean Collection for Type Cultures.

*Bacteroides vulgatus* is one of the major bacteria that constitutes intestinal microflora. It was confirmed in the present disclosure that the strain of the present disclosure is novel based on the analysis of 16s rRNA (refer to FIG. 1) and shows that the LPS pattern is very much different from the strains previously known. In particular, it has been found in the present disclosure that the present strain has the form of O-antigen that is different from previously known. O-antigen is a repetitive glycan polymer contained within LPS and is a recognition target of host antibody. Further, it has been found in the present disclosure that the LPS extracted from the strain of the present disclosure has cytotoxicity that is reduced about by half compared to that from *Vibrio vulnificus*. This is particularly advantageous when used as an inhibitor of biofilm formation.

In particular, LPS derived from the strain according to the present invention exhibits an excellent biofilm formation prevention or inhibitory effect, especially when used in combination with LTA. This prophylactic or inhibitory effect according to the present disclosure can have effect on the biofilms formed by Gram-positive and Gram-negative bacteria.

The "biofilm" of the present disclosure refers to a three-dimensional structure composed of extracellular polymeric matrix secreted by the microorganisms and bacteria. Most bacteria can adhere to the surface and proliferate thereon, in which case they form a single membrane, aggregates, or the biofilm. The biofilm can be formed on almost any type of surfaces, including biological tissues.

Such biofilms are commonly found in biological, medical and industrial environments that are commonly encountered in the environment. In the case of pathogenic bacteria that can inhabit a living body, biofilms are formed on various tissues/organs including host epithelial cells, bones, teeth, inner walls of blood vessels, various artificial implants such as catheters and implants, various medical instruments/equipment/facilities, and the like. When the biofilm is formed, the bacteria can withstand the harsh environment as well as show strong resistance to antibiotics and immune cells, making it very difficult to remove, causing chronic inflammatory diseases, and causing microbiologically induced corrosion in objects. It is known that the biofilm formation is a major cause for about 65% of all infectious diseases (Ymele-Leki and Ross, 2007, Applied and Environmental Microbiology 73 (6): 1834-41). Therefore, control of biofilm formation is very important in preventing corrosion by bacteria or preventing/treating infection by pathogenic bacteria or preventing/treating diseases.

In one embodiment, the biofilm is formed by Gram-positive bacteria. The Gram-positive bacteria include, but are not limited to *Staphylococcus aureus, Streptococcus mutans, Streptococcus pneumonia, Staphylococcus epidermidis, Enterococcus faecalis*, or *Streptococcus gordonii*, which forms biofilm. In one embodiment of the present application, the biofilm is formed by *Staphylococcus aureus, Enterococcus faecalis*, or *Streptococcus gordonii*.

In other embodiment, the biofilm is formed by Gram-negative bacteria. The Gram-negative bacteria include, but are not limited to, *Vibrio vulnificus, Vibrio cholera, Vibrio parahaemolyticus, Escherichia coli, Pseudomonas aeruginosa, Klebsiella pneumonia, Salmonella enterica, Shigella flexneri, Bacteroides vulgatus*, which forms biofilm.

In another aspect, the present disclosure relates to a composition for inhibiting or preventing biofilm formation comprising a combination of a detoxified LPS i.e., dLPS (deacylated Lipopolysaccharide), and a detoxified LTA, i.e., dLTA (deacylated Lipoteichoic acid).

The term "Lipoteichoic acid" of the present disclosure refers to a major component found with the cell wall of Gram-positive bacteria, having a teichoic acid, a bacterial copolymers of glycerol phosphate or ribitol phosphate and carbohydrates linked via phosphodiester bonds, and found within the cell membrane teichoic acid, which is a polymer of glycerol phosphoric acid, on the cell membrane. The structures of LTA vary depending on the species of Gram-positive bacteria. In one embodiment, Lipoteichoic acid is from genus *Lactobacillus*, particularly, *Lactobacillus plantarum*. As used herein, the structure of *Lactobacillus plantarum* lipoteichoic acid can be identified by nuclear magnetic resonance (NMR) and MALDI-TOF mass spectrometry, and *Lactobacillus plantarum* lipoteichoic acid is characterized by having glycolipid with three acyl chains and containing both saturated and unsaturated fatty acids. And the sugar of the glycolipid is composed of glucose and galactose.

The term "Lipopolysaccharide" of the present disclosure refers to a major component in the outer membrane of Gram-negative bacteria and consists of the hydrophobic lipid A, core oligosaccharides, and the O-antigen-specific polysaccharides (O—Ag).

The dLPS and dLTA comprised in the composition according to the present application may be comprised at the concentration (μg/ml) ratio of about 13.9:1, respectively.

The composition and method of the present disclosure can find wide applications in the field where the control of biofilm formation is required, for example, the home environment, natural environment, and medical and industrial environment. In one embodiment, the present composition and method can be advantageously used to control biofilm formation found in various artificial instruments such as medical devices, medical equipment, medical facilities/instruments, as well as various artificial implants applied to living tissues and living bodies, such as various living tissues/organs.

The present composition and method for preventing or inhibiting the biofilm formation may be prepared in various forms to suit specific need in the home, industrial, medical, and environmental fields. For example, in the form of liquids, sprays or solids containing the biofilm formation inhibitor of the present disclosure in an amount effective for the inhibition and/or prevention of biofilm formation by the target bacteria, for example for cleaning the living body as well as various equipment and instruments. Depending on the purpose, it may include additional ingredients such as, but not limited to, surfactants, detergents, fungicides, fungicides, antibiotics, mold removers, acidity regulators, dyes, and/or pigments.

In one embodiment, the composition comprising the biofilm formation preventing or inhibiting agent of the present application may be prepared in powder, coating, spray, dispensing type, capsule/tablet form and the like. These compositions may further comprise surfactants such as anionic, nonionic, zwitterionic and biological surfactants and mixtures thereof.

In one embodiment, the present composition may be prepared in the form of a personal hygiene product such as contact lens disinfectant, soap, shower gel, shampoo, or dental floss, toothpaste, dentifrice or gargle cleaner for cleaning, cleaning teeth, artificial teeth or oral cavity.

In another embodiment, the present composition may be prepared in the form of a powder, coating, spray, wipe for cleaning, cleaning medical equipment/apparatus/facilities.

In other embodiments, the present biofilm formation preventing or inhibiting agent herein can be used in industrial environments such as ships, paper metal fabrication, oil refining, food processing, or water treatment devices, and can be prepared in the form of additives, liquids, paints, and coatings. When prepared as additives, it can be used in water pipes, cooling towers, lubricants and heat exchangers.

In another aspect, the present invention relates to a method for preventing or inhibiting biofilm formation by bacteria using the present biofilm formation inhibiting or preventing agents. In the present methods. the present agents or composition may be treated on or contacted with the surface on which the bacteria are growing or may be growing or the surface may be exposed to the present agents or composition, thereby the aggregation of the bacteria or the biofilm formation can be prevented or inhibited. The contact with the bacteria includes treating the surface of the article with the agents of the present disclosure. The biofilm formation preventing or inhibiting agents may be treated in an amount effective to inhibit the desired biofilm formation, as mentioned above. The surface refers to both internal and external surfaces, and includes both solid (hard) and flexible surfaces including those derived from living organisms, as well as those used in the home, industrial, environmental, and medical fields. The hard surfaces include, but are not limited to, drainage pipes, glazed ceramics, porcelain glass, metal, wood, chromium, plastics, vinyl, and formica. Also the solid surface may also be tissue or organ derived from an organism such as skin, teeth. The solid surface may also be derived from a medical article. The medical articles include, but are not limited to, various medical facilities, equipment, instruments, temporary or permanent prosthetic implants, such as lenses, valves, pacemakers, surgical pins, insertion conduits, catheters, and the like.

The present compositions can be used in an amount effective to prevent or inhibit biofilm formation. The effective amount can be determined according to the conditions including the type of bacteria forming the biofilm, the type and area of the surface to be treated, and the desired level of reduction of the biofilm formation, the time of treatment, and the like. Appropriate concentrations may be easily selected based on the common knowledge of biofilm formation. For example, the concentration may referred to the amount effective to inhibit or prevent the biofilm formation for example, without being limited thereto, by about 100%, about 95% or more, about 90% or more, about 85% or more, or about 80% or more, about 75%, or more a about 70% or more, about 65% or more, about 50% or more, about 45% or more, about 40% or more, about 35% or more, about 30% or more, about 25% or more, about 20% or more depending on the purpose as compared to before the treatment when measured by the biofilm formation measurement method described in the Examples.

The present disclosure is further explained in more detail with reference to the following examples. These examples, however, should not be interpreted as limiting the scope of the present invention in any manner.

EXAMPLES

Example 1: Isolation and Characterization of *Bacteroides vulgatus* MGM001

*Bacteroides vulgatus* MGM001 was isolated from the feces of experimental animal ICR mouse. The strain according to the present application was deposited as KCTC13624BP Aug. 16, 2018 in the Korean Collection for Type Culture.

For the isolation, the fecal samples of ICR mouse were released/suspended in PBS buffer. Then it was spread on the plates containing *Bacteroides* Bile Esculin (BBE, Becton, Dickinson and Company, Product #221836), which is a medium for isolating strains of the genus *Bacteroides*. Then single colonies formed were streaked on a new plate for pure culture. The obtained pure cultures were then selected for 16S rRNA sequencing to identify *Bacteroides vulgatus* and isolate *Bacteroides vulgatus* MG001.

Then LPS were extracted from *B. vulgatus* MGM001, which were then detoxified as described in Example 2. The cytotoxicity thereof was determined as described in Example 3.

The analysis of the pattern of LPS of the bacteria were performed by comparing the number and sizes of the bands separated on a SDS-PAGE gel. The size of the bands can be determined by comparing them to the molecular weight marker ran on the same gel. Specifically, by comparing the total number of LPS bands obtained from each bacterial strain and the size of the first band at the bottom, it can be seen that LPS is different among strains. The bottom most band is determined as Lipid A+core oligosaccharide+one O-antigen, and from the band immediately above, the number of O-antigen is determined to increase by one. For MGM001 strain, the size of the bottom most band was in the range of about 10~16 kDa, and six bands were observed. For other *B. vulgatus* strains, the size of the bottom most bands was different from that of MGM001 (ATCC8482 was slightly lower than 23 kDa, CL 10 T00C06 was in the range of 3~6 kDa), and the number of bands were also different (ATCC8482 had at least 18 bands, CL10 T00C06 had 17 bands). Therefore, it was determined that the LPS of MGM001 of the present disclosure is different from that of other *B. vulgatus* strains.

Figure 1D:
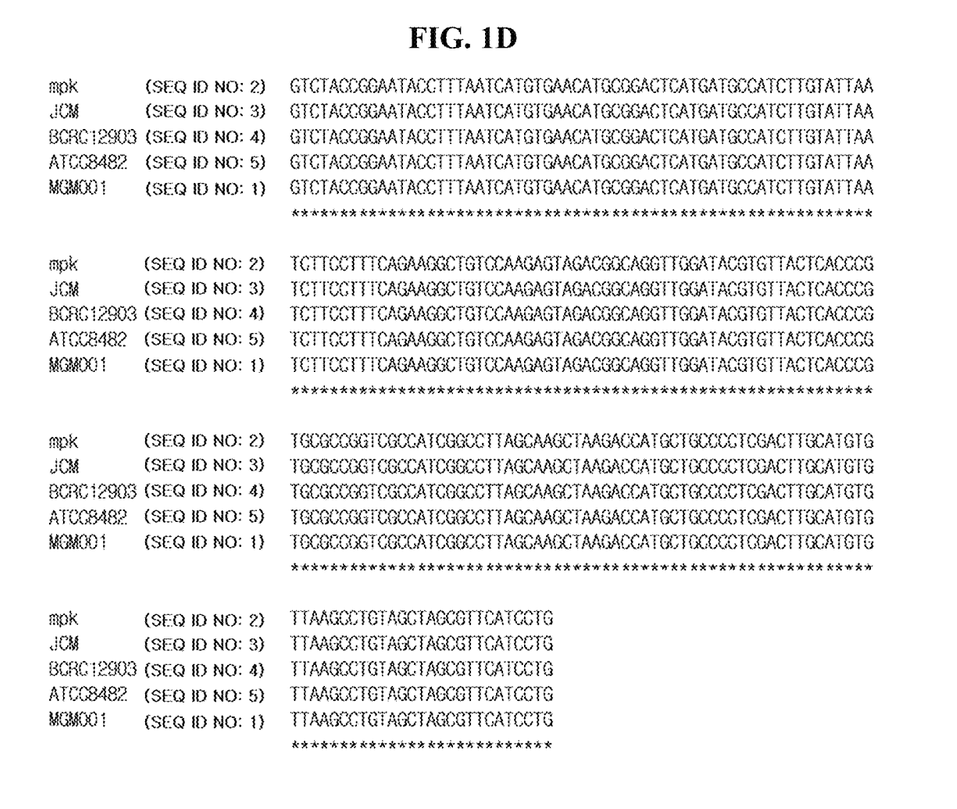
Figure 2:
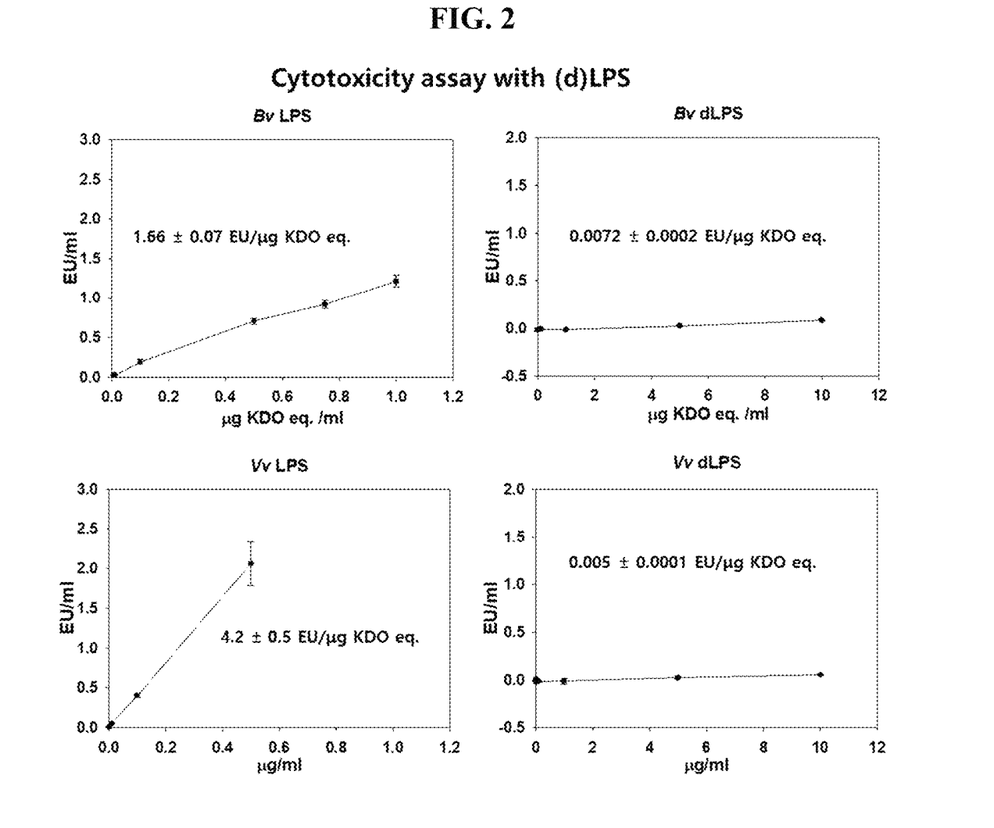
FIG. 2 shows the results of comparing the cytotoxicity of LPS and dLPS isolated from the novel strain isolated herein with those from *Vibrio vulnificus* M06-24/O (Vv), The result shows that the cytotoxicity of LPS of the strain isolated herein was reduced by half compared to that from *V. vulnificus*. This indicates that the detoxified LPS of the present disclosure can be advantageously used for preventing or inhibiting biofilm formation.

Further, the sequence of 16sRNA isolated from *B. vulgatus* MGM001 was determined and compared to that of other strains as shown in FIGS. 1A to 1D, which indicates that *B. vulgatus* MGM001 is a novel strain having 16s rRNA sequence different from other strains. Also, as shown in FIG. 2, the cytotoxicity was found to be about ½ weaker than that of conventional *V. vulnificus*. Furthermore, the pattern of LPS extracted from the novel strain of the present invention is different from the existing strains, and in particular, the shape of the O-antigen constituting the LPS is different, indicating that it is specific to the MGM001 strain of the present invention.

Information for other strains in FIG. 1 used to comparison for 16sRNA are as follows: mpk; Lange A et al. 2016, Extensive mobilome-driven genome diversification in mouse gut-associated *Bacteroides vulgatus* mpk. Genome Biol Evol 8:1197-1207; JCM 5826; Sakamoto M et al. 2010, hsp60 and 16S rRNA gene sequence relationships among species of the genus *Bacteroides* with the finding that *Bacteroides suis* and *Bacteroides tectus* are heterotypic synonyms of *Bacteroides pyogenes*. Int J Syst Evol Microbiol 60:2984-2990. BCRC 12903; Hong P Y et al. 2008, Relative abundance of *Bacteroides* spp. in stools and wastewaters as determined by hierarchical oligonucleotide primer extension. Appl Environ Microbiol 74:2882-2893.

Example 2. Extraction and Detoxification of LPS and LTA

LPS and LTA were extracted from *Bacteroides vulgatus* (MGM001) And *Lactobacillus plantarum* (KTCC1048), respectively, isolated as follows.

Example 2-1: Extraction and Detoxification of LPS

*Bacteroides vulgatus* (MGM001) was obtained by anaerobically culturing the bacteria in RCM medium for 48 hrs at 37° C. followed by centrifuging the culture. The obtained bacteria were suspended in PBS (137 mM NaCl, 2.7 mM KCl, 10 mM $Na_2HPO_4$, and 2 mM $KH_2PO_4$, pH 7.4) and incubated at 30° C. incubator with shaking at 200 rpm and then the cells were harvested by centrifuge. Then the cells were suspended TAE buffer (40 mM Tris-acetate, 2 mM EDTA, pH 8.5) and mixed 1:1 with alkaline solution (3% SDS, 50 mM Trizma base, 0.128 N NaOH) to lyse the cells. Ten mM $MgCl_2$ and DNase I (50 mg/ml) were added to the lysis solution and treated for 8 hrs, after which it was further treated with Proteinase K (200 mg/ml) for 18 hrs. Then the solution was treated with phenol-chloroform and ethanol to extract LPS (Hitchcock P J, Brown T M. (1983). J Bacteriol. 154:269-277). The extracted LPS was dissolved in 0.2 M NaOH and heated at 100° C. for 1 hr. Then the dLPS was obtained by ethanol precipitation (Fomsgaard A, Freudenberg MA and Galanos C. (1990. J Clin Microbiol. 28:2627-2631); *Bacteroides vulgatus* strain ATCC 8482 (obtained from American Type Culture Collection).

Example 2-2: Extraction and Detoxification of LTA

*Lactobacillus plantarum* (KTCC1048) was cultured anaerobically in MRS medium for 48 hrs at 37° C. and the cells were obtained by centrifuge. Then the cells obtained were suspended in 0.1 mM Sodium citrate buffer (pH 4.7) and n-butanol were added thereto at 1:1 ratio (v/v) and stirred for 30 min at RT, which were then centrifuged at 4° C. at 6000 rpm for 30 min to obtain the aqueous phase. Then 10 mM $MgCl_2$ and DNase I (50 mg/ml) and RNase A (50 mg/ml) were added thereto and treated for 8 hrs, after which it was further treated with Proteinase K(200 mg/ml) for 18 hrs. Then it was treated with phenol-chloroform and ethanol to extract LTA. The extracted LTA was treated with 0.2 M NaOH for 60 min at RT and treated with 0.2 M HCl to neutralize it. Then dLTA was extracted from the neutralized sample by phenol-chloroform and ethanol precipitation.

Figure 3:
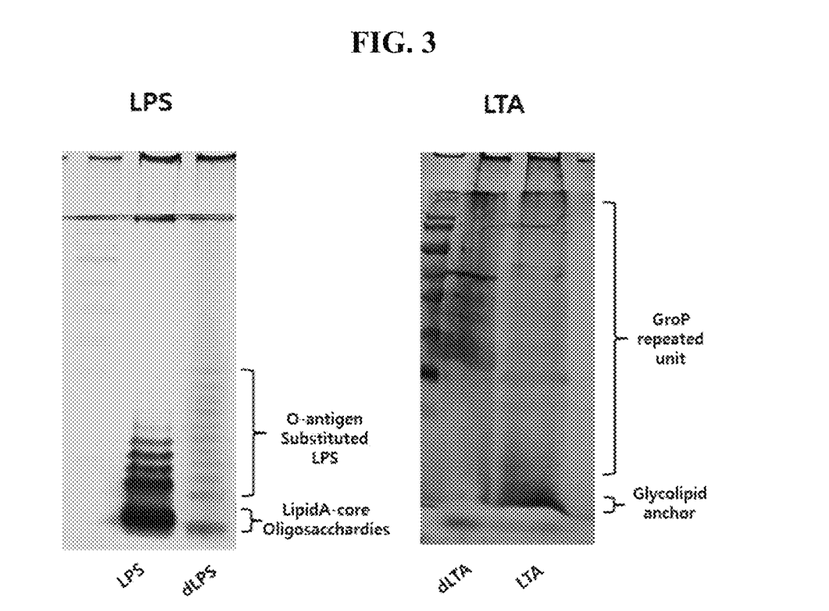
FIG. 3 shows the results of confirming that the deacylation of the LPS and LTA extracted herein was successful.

The deacylated results of LPS and LTA prepared as described in EXAMPLE 2-1 and 2-2 are shown in FIG. 3, which indicates that deacylated dLPS and dLTA with lipid parts removed from LPS and LTA were successfully prepared Example 3: Analysis of Cytotoxicity of dLPS and dLTA The 96 well plates to be used for the analysis were preincubated at 37° C. for 10 min. 50 µl of each of the dLPS and dLTA prepared at the concentration indicated were dispensed into each well of the 96 well plates. Then 50 µl of LAL agent (Pierce LAL Chromogenic Endotoxin Quantitation Kit, Thermo scientific) was added thereto and the plates were gently rocked and incubated at 37° C. for 10 min. Then 100 µl of a chromogenic substrate solution previously set at 37° C. was added into each well of the plates, which was then gently rocked and incubated at 37° C. for 6 min. Then 100 µl of termination solution was added to each well of the plate and gently rocked. Subsequently, absorbance of each well was measured at 405 nm using spectrophotometer.

Figure 4:
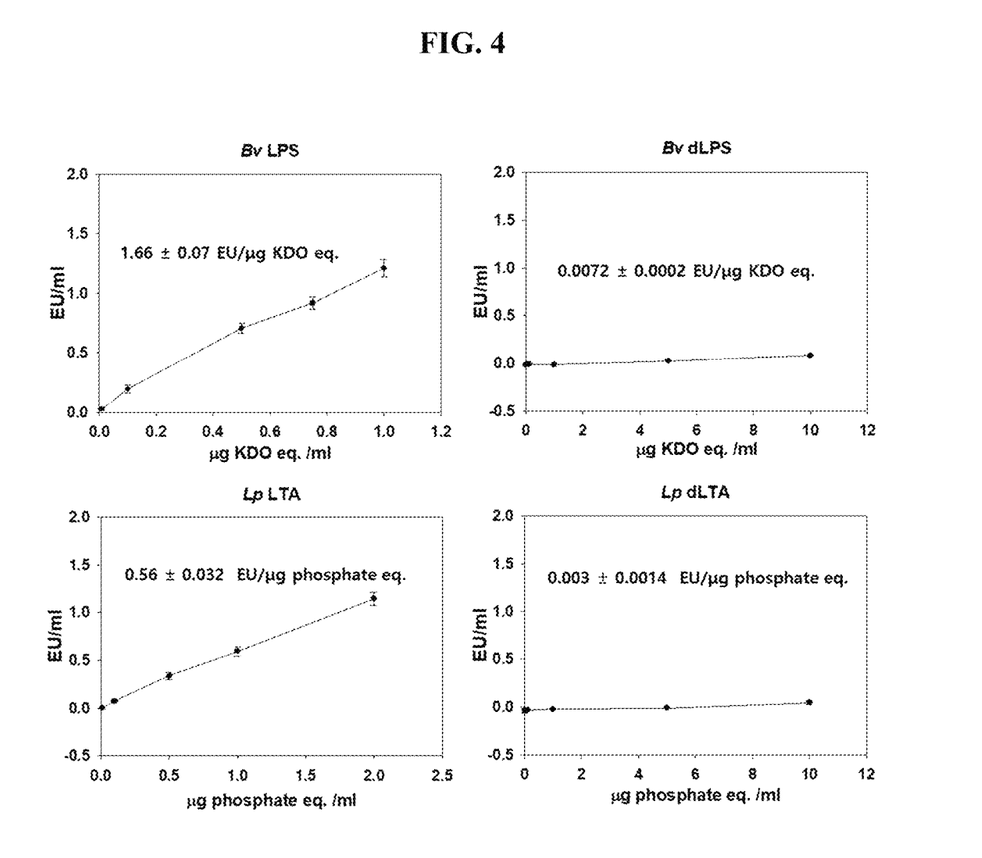
FIG. 4 shows the results of confirming that the cytotoxicity of the deacylated LPS/LTA is significantly lowered.

Results are shown in FIG. 4. As shown in FIG. 4, LPS and LTA from which lipid parts were not removed showed cytotoxicity (LPS: 1.66 EU/µg KDO eq., LTA: 0.56 EU/µg phosphate eq.). However, when the lipid parts each of LPS and LTA were removed, the cytotoxicity was significantly lowered (dLPS: 0.0072 EU/µg KDO eq., dLPS: 0.003 EU/µg phosphate eq.).

Example 4: Analysis of the Effect of Detoxified dLPS and dLTA and Cocktail of dLPS+dLTA on the Biofilm Formation on Various Matrixes The anti-biofilm formation effect of LPS and LTA with lipid parts removed as described in Example 3 and the effect of the combination of dLPS and dLTA were analyzed using pathogenic bacteria [Gram-negative (*V. vulnificus, P. aeruginosa*) and Gram-positive (*S. aureus, L. monocytogenes*)]. The effect on the biofilm formation was tested on the various materials found in real life.

Specifically, the bacteria used in the present Example were as follows: *Vibrio vulnificus* M06-24/O, *Pseudomonas aeruginosa* pRO1957, *Staphylococcus aureus* ATCC6538, *Listeria monocytogenes* ATCC19117. The above bacteria were cultured in LB medium (tryptone 1%, yeast extract 0.5%, NaCl 1%) at 30° C. The cultured bacteria, *V. vulnificus, P. aeruginosa, S. aureus* and *L. monocytogenes* were inoculated into the chamber containing a plate (2.5 cm×7 cm in size) each made of porcelain, aluminum, brass, stainless steel and acryl and the anti-biofilm effects of dLTA and dLPS prepared as described in Example 1 were tested.

For this, dLPS and dLTA were added at the concentration range of 104~5200 µg/ml, and 7.5~375 µg/ml, respectively and incubated aerobically for 48 hrs at 30° C. After 48 hrs, the biofilm formed in each material was stained with 1% crystal violet and washed once with distilled water, which were then treated with 100% EtOH and analyzed by measuring absorbance at 550 nm using spectrometer. The proliferation or growth of the bacteria was analyzed by measuring the absorbance at 595 nm. Results are shown in Table 1.

TABLE 1

| Bacteria | Treated with | $EC_{50\ (\mu g/ml)}$ | | | | | |
|---|---|---|---|---|---|---|---|
| | | Porcelain | Aluminum | Brass | Glass | Stainless | Acryl |
| V. vulnificus (−) | dLPS | 679.8 (±230.8) | 176.3 (±37.5) | 113.3 (±15.1) | 280.8 (±21.4) | 478.3 (±51.3) | No effect |
| S. aureus (+) | dLTA | 13.2 (±2.9) | 20.1 (±6.9) | 16.2 (±1.6) | 27.2 (±7.8) | 43 (±8.5) | No effect |
| V. vulnificus (−) + P. deruginosa (−) | dLPS | 426.3 (±301.7) | 284.4 (±97.9) | 287.9 (±114.9) | 308.8 (±221.7) | 297.3 (±132.5) | No effect |
| S. aureus (+) + L. monocytogenes (+) | dLTA | 8.46 (±0.87) | 9.08 (±1.71) | 10.7 (±1.79) | 8.18 (±0.77) | 9.72 (±2.5) | No effect |
| V. Vulnificus (−) + S. aureus (+) | Cocktail dLPS | 62.7 (±7.2) | 82.4 (±28.3) | 64 (±10.3) | 66.4 (±4.4) | 111.8 (±25.7) | No effect |
| | dLTA | 4.5 (±0.5) | 5.9 (±2.0) | 4.6 (±0.7) | 4.8 (±0.3) | 8.1 (±1.9) | |

As a result of adding dLPS at various concentrations to the biofilms produced in various matrix by *V. vulnificus*, the Gram-negative pathogenic bacterium, it was confirmed that it had an anti-biofilm formation effect. As a result of adding dLTA at various concentrations to the biofilms produced in various matrix by *S. aureus*, the Gram-positive pathogenic bacterium, it was confirmed that there was an anti-biofilm formation effect.

In addition, the addition of dLPS showed anti-biofilm formation effect on the biofilms produced in various matrix by the mixture of two Gram-negative pathogenic bacteria (*V. vulnificus*, and *P. aeruginosa*). Also the addition of dLTA showed anti-biofilm formation effect on the biofilms produced in various matrix by the mixture of two Gram-positive pathogenic bacteria (*S. aureus, L. monocytogenes*)

Further, it was shown that the combination of 'dLPS+ dLTA cocktail' showed synergistic effect in inhibiting biofilm formation at various concentrations added. In particular, when half maximal effective concentration ($EC_{50}$) of each of dLPS and dLTA were calculated, the anti-biofilm effect was increased by 2~11 times depending on the matrix/material used in case of dLPS and about 3~6 times in case of dLTA (See Table 1).

Based on the results, it was found that the ratio of 13.9:1 of dLPS and dLTA in 'dLPS+dLTA cocktail' showed synergistic effect in inhibiting biofilm formation when each was used separately, showed superior anti-biofilm formation effect on various materials found in real life except on acrylic material.

DEPOSIT INFORMATION

Depository Institution: Korean Collection for Type Cultures, located 181, Ipsin-gil, Jeongeup-si, Jeollabuk-do 56212 Republic of Korea
Deposit Number: KCTC 13624BP
Date of Deposit: Aug. 16, 2018
The access to the above biological deposit is irrevocably granted for the term of the patent issuing from the application.

What is claimed is:

1. A method of inhibiting or preventing biofilm formation comprising contacting the composition with Gram-positive or Gram-negative bacteria, wherein the composition comprises dLPS (deacylated Lipopolysaccharide) and dLTA (deacylated Lipoteichoic acid) in combination, wherein the dLPS is from *Bacteroides vulgatus* MGM001 (*Bacteroides vulgatus* MGM001) strain deposited as KCTC13624BP at Korean Collection for Type Cultures.

2. The method of claim 1, wherein the dLTA is from *Lactobacillus plantarum*.

3. The method of claim 1, wherein the dLPS and dLTA are comprised at the concentration ratio of 13.9:1(µg/ml).

4. The method of claim 1, wherein the biofilm is produced from Gram-negative bacteria *Vibrio vulnificus*, or *Pseudomonas aeruginosa*.

5. The method of claim 1, wherein the biofilm is produced from Gram-positive bacteria, *S. aureus*, or *L. monocytogenes*.

6. The method of claim 1, wherein the contacting includes treating the surface with the composition, wherein the surface is selected from the group consisting of Glaze ceramic, porcelain, glass, metal, wood, chrome, plastic, vinyl and formica, and wherein the surface is not made of acryl.

7. The method of claim 2, wherein the dLPS and dLTA are comprised at the concentration ratio of 13.9:1(µg/ml).

* * * * *

SEQUENCE LISTING

```
<160> NUMBER OF SEQ ID NOS: 5

<210> SEQ ID NO 1
<211> LENGTH: 1466
<212> TYPE: DNA
<213> ORGANISM: Bacteroides vulgatus
<220> FEATURE:
<221> NAME/KEY: misc_feature
<222> LOCATION: (1)...(1466)
<223> OTHER INFORMATION: strain MGM001

<400> SEQUENCE: 1
ccttacttca ggtaccccg gctcccatgg cttgacgggc ggtgtgtaca aggcccggga      60
acgttgacga cttagcccca gtcaccagtt ttaccctagg gcgctcctcg cggttacgca     120
ttcaccgcgc cgtggctgat gcgcgattac tagcgaatcc agcttcgtgg agtcgggttg     180
cagactccag tccgaactga gagaggtttt tgggattggc atccactcgc gtggtagcgg     240
ccctctgtac ccccattgt aacacgtgtg tagcccggga cgtaagggcc gtgctgattt      300
gacgtcatcc ccaccttcct cacatcttac gatgcagtc ttgtcagagt cctcagcaga     360
acctgttagt aactgacaac aagggttgcg ctcgttatgg cacttaagcc gacacctcac     420
ggcacgagct gacgacaacc atgcagcacc ttcacagatg ccttgcggct tacggctttc     480
```

| | |
|---|---|
| accgtaattc atctgcaatt taagcccggg taaggttcct cgcgtatcat cgaattaaac | 540 |
| cacatgttcc tccgcttgtg cgggccccg tcaattcctt tgagtttcac cgttgccggc | 600 |
| gtactcccca ggtggaatac ttaacgcttt cgcttggccg cttgccgtat atcgcaaaca | 660 |
| gcgagtattc atcgtttacc gtgtggacta ccagggtatc taatcctgtt tgatacccac | 720 |
| actttcgagc ctcaatgtca gttgcagctt agcaggctgc cttcgcaatc ggagttcttc | 780 |
| gtgatatcta agcatttcac cgctacacca cgaattccgc ctgcctcaac tgcactcaag | 840 |
| atatccagta tcaactgcaa ttttacggtt gagccgcaaa ctttcacaac tgacttaaac | 900 |
| atccatctac gctcccttta aacccaataa atccggataa cgctcggatc ctccgtatta | 960 |
| ccgcggctgc tggcacggag ttagccgatc cttattcata aagtacatgc aaacgggtat | 1020 |
| ccatacccga ctttattcct ttataaaaga agtttacaac ccatagggca gtcatccttc | 1080 |
| acgctacttg gctggttcag gctctcgccc attgaccaat attcctcact gctgcctccc | 1140 |
| gtaggagttt ggaccgtgtc tcagttccaa tgtgggggac cttcctctca gaaccccctat | 1200 |
| ccatcgaaga ctaggtgggc cgttaccccg cctactatct aatggaacgc atccccatcg | 1260 |
| tctaccggaa tacctttaat catgtgaaca tgcggactca tgatgccatc ttgtattaat | 1320 |
| cttcctttca gaaggctgtc caagagtaga cggcaggttg gatacgtgtt actcaccgt | 1380 |
| gcgccggtcg ccatcggcct tagcaagcta agaccatgct gccctcgac ttgcatgtgt | 1440 |
| taagcctgta gctagcgttc atcctg | 1466 |

<210> SEQ ID NO 2
<211> LENGTH: 1467
<212> TYPE: DNA
<213> ORGANISM: Bacteroides vulgatus
<220> FEATURE:
<221> NAME/KEY: misc_feature
<222> LOCATION: (1)..(1467)
<223> OTHER INFORMATION: strain mpk

<400> SEQUENCE: 2

| | |
|---|---|
| ccttgttacg acttagcccc agtcaccagt tttaccctag ggcgctcctc gcggttacgc | 60 |
| acttcaggta cccccggctc ccatggcttg acgggcggtg tgtacaaggc ccgggaacgt | 120 |
| attcaccgcg ccgtggctga tgcgcgatta ctagcgaatc cagcttcgtg gagtcgggtt | 180 |
| gcagactcca gtccgaactg agagaggttt tggggattgg catccactcg cgtggtagcg | 240 |
| gccctctgta cccccattg taacacgtgt gtagcccgg acgtaagggc cgtgctgatt | 300 |
| tgacgtcatc cccaccttcc tcacatctta cgatggcagt cttgtcagag tcctcagcgg | 360 |
| aacctgttag taactgacaa caagggttgc gctcgttatg gcacttaagc cgacacctca | 420 |
| cggcacgagc tgacgacaac catgcagcac cttcacagat gccttgcggc ttacggcttt | 480 |
| caccgtaatt catctgcaat ttaagcccgg gtaaggttcc tcgcgtatca tcgaattaaa | 540 |
| ccacatgttc ctccgcttgt gcgggcccc gtcaattcct ttgagtttca ccgttgccgg | 600 |
| cgtactcccc aggtggaata cttaacgctt tcgcttggcc gcttgcagta tatcgcaaac | 660 |
| agcgagtatt catcgtttac cgtgtggact accagggtat ctaatcctgt ttgatacccac | 720 |
| cactttcgag cctcaatgtc agttgcagct tagcaggctg ccttcgcaat cggagttctt | 780 |
| cgtgatatct aagcatttca ccgctacacc acgaattccg cctgcctcaa ctgcactcaa | 840 |
| gatatccagt atcaactgca attttacggt tgagccgcaa actttcacaa ctgacttaaa | 900 |
| catccatcta cgctcccttt aaacccaata atccggata cgctcggat cctccgtatt | 960 |
| accgcggctg ctggcacgga gttagccgat ccttattcat aaagtacatg caaacgggta | 1020 |

| | |
|---|---:|
| tccatacccg actttattcc tttataaaag aagtttacaa cccatagggc agtcatcctt | 1080 |
| cacgctactt ggctggttca ggctctcgcc cattgaccaa tattcctcac tgctgcctcc | 1140 |
| cgtaggagtt tggaccgtgt ctcagttcca atgtggggga ccttcctctc agaacccta | 1200 |
| tccatcgaag actaggtggg ccgttacccc gcctactatc taatggaacg catccccatc | 1260 |
| gtctaccgga atacctttaa tcatgtgaac atgcggactc atgatgccat cttgtattaa | 1320 |
| tcttcctttc agaaggctgt ccaagagtag acggcaggtt ggatacgtgt tactcacccg | 1380 |
| tgcgccggtc gccatcggcc ttagcaagct aagaccatgc tgcccctcga cttgcatgtg | 1440 |
| ttaagcctgt agctagcgtt catcctg | 1467 |

<210> SEQ ID NO 3
<211> LENGTH: 1467
<212> TYPE: DNA
<213> ORGANISM: Bacteroides vulgatus
<220> FEATURE:
<221> NAME/KEY: misc_feature
<222> LOCATION: (1)..(1467)
<223> OTHER INFORMATION: strain JCM

<400> SEQUENCE: 3

| | |
|---|---:|
| ccttgttacg acttagcccc agtcaccagt tttaccctag ggcgctcctc gcggttacgc | 60 |
| acttcaggta cccccggctc ccatggcttg acgggcggtg tgtacaaggc ccggaacgt | 120 |
| attcaccgcg ccgtggctga tgcgcgatta ctagcgaatc cagcttcgtg gagtcgggtt | 180 |
| gcagactcca gtccgaactg agagaggttt tggggattgg catccactcg cgtggtagcg | 240 |
| gccctctgta cccccccattg taacacgtgt gtagcccggg acgtaagggc cgtgctgatt | 300 |
| tgacgtcatc cccaccttcc tcacatctta cgatggcagt cttgtcagag tcctcagcat | 360 |
| aacctgttag taactgacaa caagggttgc gctcgttatg gcacttaagc cgacacctca | 420 |
| cggcacgagc tgacgacaac catgcagcac cttcacagat gccttgcggc ttacggcttt | 480 |
| caccgtaatt catctgcaat ttaagcccgg gtaaggttcc tcgcgtatca tcgaattaaa | 540 |
| ccacatgttc ctccgcttgt gcgggccccc gtcaattcct ttgagtttca ccgttgccgg | 600 |
| cgtactcccc aggtggaata cttaacgctt tcgcttggcc gcttgccgta tatcgcaaac | 660 |
| agcgagtatt catcgtttac cgtgtggact accagggtat ctaatcctgt ttgatacca | 720 |
| cactttcgag cctcaatgtc agttgcagct tagcaggctg ccttcgcaat cggagttctt | 780 |
| cgtgatatct aagcatttca ccgctacacc acgaattccg cctgcctcaa ctgcactcaa | 840 |
| gatatccagt atcaactgca attttacggt tgagccgcaa actttcacaa ctgacttaaa | 900 |
| catccatcta cgctcccttt aaacccaata aatccggata acgctcggat cctccgtatt | 960 |
| accgcggctg ctggcacgga gttagccgat ccttattcat aaagtacatg caaacgggta | 1020 |
| tccatacccg actttattcc tttataaaag aagtttacaa cccatagggc agtcatcctt | 1080 |
| cacgctactt ggctggttca ggctctcgcc cattgaccaa tattcctcac tgctgcctcc | 1140 |
| cgtaggagtt tggaccgtgt ctcagttcca atgtggggga ccttcctctc agaacccta | 1200 |
| tccatcgaag actaggtggg ccgttacccc gcctactatc taatggaacg catccccatc | 1260 |
| gtctaccgga atacctttaa tcatgtgaac atgcggactc atgatgccat cttgtattaa | 1320 |
| tcttcctttc agaaggctgt ccaagagtag acggcaggtt ggatacgtgt tactcacccg | 1380 |
| tgcgccggtc gccatcggcc ttagcaagct aagaccatgc tgcccctcga cttgcatgtg | 1440 |
| ttaagcctgt agctagcgtt catcctg | 1467 |

<210> SEQ ID NO 4
<211> LENGTH: 1467
<212> TYPE: DNA
<213> ORGANISM: Bacteroides vulgatus
<220> FEATURE:
<221> NAME/KEY: misc_feature
<222> LOCATION: (1)..(1467)
<223> OTHER INFORMATION: strain BCRC 12903

<400> SEQUENCE: 4

| | | | | | |
|---|---|---|---|---|---|
| ccttgttacg | acttagcccc | agtcaccagt | tttaccctag | ggcgctcctc | gcggttacgc | 60 |
| acttcaggta | cccccggctc | ccatggcttg | acgggcggtg | tgtacaaggc | ccgggaacgt | 120 |
| attcaccgcg | ccgtggctga | tgcgcgatta | ctagcgaatc | cagcttcgtg | gagtcgggtt | 180 |
| gcagactcca | gtccgaactg | agagaggttt | tggggattgg | catccactcg | cgtggtagcg | 240 |
| gccctctgta | cccccattg | taacacgtgt | gtagccccgg | acgtaagggc | cgtgctgatt | 300 |
| tgacgtcatc | cccaccttcc | tcacatctta | cgatggcagt | cttgtcagag | tcctcagcat | 360 |
| gacctgttag | taactgacaa | caagggttgc | gctcgttatg | cacttaagc | cgacacctca | 420 |
| cggcacgagc | tgacgacaac | catgcagcac | cttcacagat | gccttgcggc | ttacggcttt | 480 |
| caccgtaatt | catctgcaat | ttaagcccgg | gtaaggttcc | tcgcgtatca | tcgaattaaa | 540 |
| ccacatgttc | ctccgcttgt | gcgggccccc | gtcaattcct | ttgagtttca | ccgttgccgg | 600 |
| cgtactcccc | aggtgaata | cttaacgctt | tcgcttggcc | gcttgccgta | tatcgcaaac | 660 |
| agcgagtatt | catcgtttac | cgtgtggact | accagggtat | ctaatcctgt | ttgatcccca | 720 |
| cactttcgag | cctcaatgtc | agttgcagct | tagcaggctg | ccttcgcaat | cggagttctt | 780 |
| cgtgatatct | aagcatttca | ccgctacacc | acgaattccg | cctgcctcaa | ctgcactcaa | 840 |
| gatatccagt | atcaactgca | attttacggt | tgagccgcaa | actttcacaa | ctgacttaaa | 900 |
| catccatcta | cgctccctt | aaacccaata | aatccggata | acgctcggat | cctccgtatt | 960 |
| accgcggctg | ctggcacgga | gttagccgat | ccttattcat | aaagtacatg | caaacgggta | 1020 |
| tccatacccg | actttattcc | tttataaaag | aagtttacaa | cccataggggc | agtcatcctt | 1080 |
| cacgctactt | ggctggttca | ggctctcgcc | cattgaccaa | tattcctcac | tgctgcctcc | 1140 |
| cgtaggagtt | tggaccgtgt | ctcagttcca | atgtggggga | ccttcctctc | agaaccccta | 1200 |
| tccatcgaag | actaggtggg | ccgttacccc | gcctactatc | taatgaaacg | catccccatc | 1260 |
| gtctaccgga | atacctttaa | tcatgtgaac | atgcggactc | atgatgccat | cttgtattaa | 1320 |
| tcttcctttc | agaaggctgt | ccaagagtag | acggcaggtt | ggatacgtgt | tactcacccg | 1380 |
| tgcgccggtc | gccatcggcc | ttagcaagct | aagaccatgc | tgcccctcga | cttgcatgtg | 1440 |
| ttaagcctgt | agctagcgtt | catcctg | | | | 1467 |

<210> SEQ ID NO 5
<211> LENGTH: 1467
<212> TYPE: DNA
<213> ORGANISM: Bacteroides vulgatus
<220> FEATURE:
<221> NAME/KEY: misc_feature
<222> LOCATION: (1)..(1467)
<223> OTHER INFORMATION: strain ATCC 8482

<400> SEQUENCE: 5

| | | | | | |
|---|---|---|---|---|---|
| ccttgttacg | acttagcccc | agtcaccagt | tttaccctag | ggcgctcctc | gcggttacgc | 60 |
| acttcaggta | cccccggctc | ccatggcttg | acgggcggtg | tgtacaaggc | ccgggaacgt | 120 |
| attcaccgcg | ccgtggctga | tgcgcgatta | ctagcgaatc | cagcttcgtg | gagtcgggtt | 180 |

```
gcagactcca gtccgaactg agagaggttt tgggattgg catccactcg cgtggtagcg      240
gccctctgta cccccattg taacacgtgt gtagccccgg acgtaagggc cgtgctgatt      300
tgacgtcatc cccaccttcc tcacatctta cgatggcagt cttgtcagag tcctcagcag     360
aacctgttag taactgacaa caagggttgc gctcgttatg gcacttaagc cgacacctca     420
cggcacgagc tgacgacaac catgcagcac cttcacagat gccttgcggc ttacggcttt     480
caccgtaatt catctgcaat ttaagcccgg gtaaggttcc tcgcgtatca tcgaattaaa     540
ccacatgttc ctccgcttgt gcgggccccc gtcaattcct ttgagtttca ccgttgccgg     600
cgtactcccc aggtggaata cttaacgctt tcgcttggcc gcttgccgta tatcgcaaac     660
agcgagtatt catcgtttac cgtgtggact accagggtat ctaatcctgt ttgatacccca    720 cactttcgag cctcaatgtc agttgcagct tagcaggctg ccttcgcaat cggagttcct     780
cgtgatatct aagcatttca ccgctacacc acgaattccg cctgcctcaa ctgcactcaa     840
gatatccagt atcaactgca attttacggt tgagccgcaa actttcacaa ctgacttaaa     900
catccatcta cgctcccttt aaacccaata atccggata acgctcggat cctccgtatt      960
accgcggctg ctggcacgga gttagccgat ccttattcat aaagtacatg caaacgggta    1020
tgcatacccg actttattcc tttataaaag aagtttacaa cccatagggc agtcatcctt    1080
cacgctactt ggctggttca ggctctcgcc cattgaccaa tattcctcac tgctgcctcc    1140
cgtaggagtt tggaccgtgt ctcagttcca atgtggggga ccttcctctc agaacccta    1200 tccatcgaag actaggtggg ccgttacccc gcctactatc taatggaacg catccccatc    1260
gtctaccgga ataccttaa tcatgtgaac atgcggactc atgatgccat cttgtattaa     1320
tcttcctttc agaaggctgt ccaagagtag acggcaggtt ggatacgtgt tactcacccg    1380
tgcgccggtc gccatcggcc ttagcaagct aagaccatgc tgcccctcga cttgcatgtg    1440
ttaagcctgt agctagcgtt catcctg                                          1467
```